United States Patent [19]

Fakhouri

[11] 4,172,703
[45] Oct. 30, 1979

[54] OXIDATIVE BROWN HAIR DYE

[75] Inventor: Najib M. Fakhouri, Palo Alto, Calif.

[73] Assignee: Syntex (USA) Inc., Palo Alto, Calif.

[21] Appl. No.: 930,832

[22] Filed: Aug. 3, 1978

[51] Int. Cl.$^2$ ................................................ A61K 7/13
[52] U.S. Cl. ........................................ 8/10.2; 8/11; 8/32; 8/79
[58] Field of Search .................. 8/10.2, 11, 32, 79

[56] References Cited

U.S. PATENT DOCUMENTS

| | | | |
|---|---|---|---|
| 3,128,232 | 4/1964 | Wilmsmann et al. | 8/10.2 |
| 3,415,608 | 12/1968 | Tucker | 8/10.2 |
| 3,536,436 | 10/1970 | Lange | 8/10.2 |
| 3,630,655 | 12/1971 | Berth et al. | 8/11 |
| 3,931,912 | 1/1976 | Hsiung | 8/79 X |
| 4,003,699 | 1/1977 | Rose et al. | 8/10.2 |
| 4,010,872 | 3/1977 | Lozano et al. | 8/79 X |

OTHER PUBLICATIONS

Proc. Nat. Acad. Sci., vol. 72, No. 6, pp. 2423–2427, Jun. 1975.

Primary Examiner—James O. Thomas, Jr.
Assistant Examiner—Vera C. Clarke
Attorney, Agent, or Firm—Tom M. Moran; Joseph I. Hirsch

[57] ABSTRACT

This invention is a composition useful for dyeing keratinous fiber brown without using o-, m- or p-phenylenediamine, 2,4-diaminoanisol or nitro compounds. The composition consists essentially of 1,5-dihydroxynaphthalene, m-aminophenol, p-aminodiphenylamine or a suitable acid addition salt thereof, a suitable modifier, a suitable coupler and a suitable base. This composition in combination with an oxidizing agent dyes hair brown.

13 Claims, No Drawings

OXIDATIVE BROWN HAIR DYE

BACKGROUND OF THE INVENTION

This invention relates to a dye composition for dyeing keratinous fiber brown. More specifically, the composition is essentially free of o-, m- or p-phenylenediamine, 2,7-diaminoanisole and nitro compounds. Even more specifically the invention relates to a composition consisting of 1,5-dihydroxynaphthalene, m-aminophenol, p-aminodiphenylamine or a suitable acid addition salt thereof, a suitable modifier, a suitable coupler and a sufficient amount of a suitable base. When this composition is mixed with a effective amount of oxidizing agent and applied to keratinous fiber, particularly human hair, the fiber is dyed brown.

PRIOR ART

It is generally known that commercial oxidative hair dyes require the presence of o-, m- or p-phenylenediamine or 2,4-diaminoanisole and the direct dyes require the presence of nitro compounds. However, in recent years it has been found that these compounds may exhibit a mutagenic reaction in the Ames test either in the oxidized or unoxidized state. See Ames, et al., "Hair Dyes are Mutagenic: Identification of a Variety of Mutagenic Ingredients" PROC. NAT. ACAD. SCI. U.S.A., 72, No. 6, pp. 2423–2427, June, 1975.

While the individual compounds of this invention have been known for many years, these compounds have been used in association with o-,m and p-phenylenediamine, 2,4-diaminoamisole but have never been employed by themselves because it was thought that the o-, m- or p-phenylenediamines or 2,4-diaminoanisole were necessary to form the desired shades of brown. For discussion of the role of o-, m- or p-phenylenediamine and 2,4-diaminoamisole as dye-forming intermediates in oxidation dyes see *The Chemistry and Manufacture of Cosmetics*, Vol. IV, 2nd Edition, edited by Maison G. de Navarre, pages 841–920.

It has now been discovered that a specific unique combination of previously known compounds has been found to give excellent dyes for dyeing keratinous fibers brown without using any o-, m- or p-phenylenediamine, 2,4-diaminoamisole or nitro compounds.

SUMMARY OF THE INVENTION

One aspect of this invention is a composition for dyeing keratinous fiber brown. The composition is essentially free of o-, m- or p-phenylenediamine, 2,4-diaminoanisole and nitro compounds. The composition consists essentially of about 0.1 to 4.0 parts by weight 1,5-dihydroxynaphthalene, about 0.2 to 2.5 parts by weight m-aminophenol, about 0.01 to 1.5 parts by weight p-aminodiphenylamine or a suitable acid addition salt thereof, about 0.5 to 15.0 parts by weight of a suitable modifier, about 0.5 to 7.5 parts by weight of a suitable coupler, and a sufficient amount of a suitable base to make up a total of 100 parts by weight of such composition.

Another aspect of the invention is a combination of the above composition with a suitable oxidizing agent. This combination may be an actual mixture of the two or may be a combination of the composition and the oxidizing agent in two separate containers together in a sngle package.

Still another aspect of the invention is a process for dyeing keratinous fibers, particularly human hair, brown which comprises contacting the fibers with an effective amount of a mixture of the composition and an oxidizing agent for a time sufficient to effect dyeing of the fibers.

FURTHER DESCRIPTION AND PREFERRED EMBODIMENTS

The following table gives the operable ranges in parts by weight (pbw) for each of the components of the novel composition of the invention as well as the optimum ranges for each of the components.

|  | Operable (pbw) | Optimum (pbw) |
| --- | --- | --- |
| 1,5-dihydroxy-naphthalene | 0.1–4.0 | .25–2.5 |
| m-aminodiphenol | 0.1–2.5 | 0.2–2.0 |
| p-aminophenyl-amine (salt) | 0.01–1.5 | 0.5–1.0 |
| modifier | 1.0–15.0 | 1.2–11.0 |
| coupler | 0.5–7.5 | 0.6–5.0 |
| base | q.s | q.s |

The three essential compounds in the composition of this invention are:

(I) 1,5-dihydroxynaphthalene, (II) m-aminophenol and (III) p-aminodiphenylamine or a suitable acid addition salt thereof as represented by the following formulas:

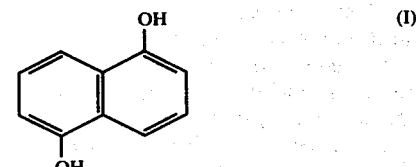

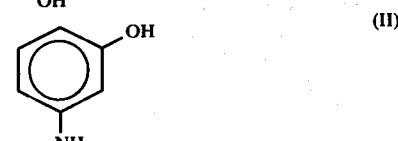

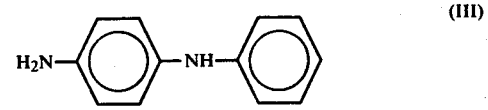

wherein (HX) represents an optional suitable acid. Suitable acid addition salts include those salts formed by reacting any appropriate inorganic or organic acid which forms a salt which is substantially non-toxic, non-irritating and still effective at the level employed. Particularly useful are the inorganic acid addition salts such as the hydrochloride, sulfates, hydrobromides, and the like. Preferred are the sulfates. Each compound may be readily prepared by means known in the art or are available through chemical outlets such as Aldrich Chemical C., Inc. The dye base which is used in the composition of this invention can be any suitable, compatible base which is generally known in the art, and will contain several components which may include a fatty acid in the form of soap, synthetic detergents, a gelling or thickening agent, a solvent, a leveling agent, a hair conditioning agent and other additives such as antioxidants, oxidation, retarders, chelating agents, pH adjusters and a perfume. In many cases the component which would fall into one category also falls into another category. Thus a fatty acid used in a base which uses ammonia as the pH adjuster may appear as ammonium oleate and thus act as a surfactant. Representative bases may be prepared employing the principles set forth in *The Chemistry and Manufacture of Cosmetics,* ibid.

Suitable fatty acids include oleic acids, palmitic acid, stearic acid, lauric acid and coconut fatty acids. NoOrmally these are used as the ammonium salt. These generally are good solvents and aid in dispersion of the dye intermediates and other ingredients in the product.

The surfactants used in the base may be on-ionic, anionic, amphoteric or combinations thereof. The surfactants serve as penetrants, dye dispersing agents, coupling agents, foam and cleansing agents (in shampoo—in colors) and they are often an essential part of the gelation system. Surfactants may include higher alcohol sulfates, ethoxylated nonylphenols, ethoxylated fatty eters, amphoterics, and the like. Particularly valuable is polyethylene glycol p-nonylphenol ether having four ethylene glycol units (IGEPAL® CO-430), polyethylene glycol (3) lauryl amide (Amidox L$_2$) and ammonium lauryl sulfate (Carsonal ALS.)

Gelling agents can be employed if a gel is desired for the base. In this case a fatty alcohol such as oleyl alcohol can be employed. Ethoxylated fatty alcohol may also be used along with alkylol amides. Gelling agents serve as thickeners, solubilizers an foam stabilizers. Oleyl alcohol has been found to be particularly valuable.

Solvents are employed in the base both to solubilize the dye intermediates as well as the water immisible components in the dye base. The referred solvents are the lower alcohols, glycols, and glycol ethers. For example, ethanol, propylene glycol, isopropyl alcohol and glycerine. Glycerine also acts as a humectant. Isopropanol, propylene glycol, an glycerine are preferred.

Leveling agents as such are seldom included in the dye base composition because many of the other ingredients perform this function, for example any of the solvents are useful as leveling agents. Fatty alcohols, fatty esters, alkylol amides and glycols all act to slow down the fusion of the intermediates into the hair and level absorbtion of the colors.

Many of the ingredients already mentioned also serve as hair conditioning agents. Other ingredients that can be used specifically for this purpose not mentioned hereinbefore include lanolin derivatives, proteins and polyvinylpyrrolidone.

Antioxidants are often added to the base to prevent air oxidation and the resulting deterioration of the product. Generally the most widely used antioxidants are the alkali metal sulfites, BHA or BHT, specifically sodium sulfite. The amount of the antioxidant used is sufficient to protect the product during the manufacture and to take care of oxygen in the head space of the bottle. Generally this amount is less than 1% and usually is not more than 0.5%. Other antioxidants include certain mercaptans (such as thioglycolic acid) ascorbic acid and 2,3-dihydroxynaphthalene.

In addition to the antioxidant, other components may be added as oxidation retarders. If oxidation takes place too rapidly before adequate diffusion of the dye intermediates into the hair can take place, weaker and uneven dyeing may result. Thus, additives are included which slow down the oxidation somewhat so that the color is developed only after the dye is sufficiently diffused into the hair. Antioxidants will act as retarders in certain instances, but specific retarders may be included such as polyhydroxyphenols, 1-phenyl-3-methyl-5-pyrazolone and the like.

Also included in the base may be chelating agents which are used to tie up trace quantities of heavy metals which can catalyze the decomposition of the peroxide once the peroxide is mixed with the dye. Generally the most useful chelating agents are the di-, tri- or tetrasodium salt of ethylenediaminetetraacetic acid (EDTA).

The dye base and final dye composition is preferably quite alkaline having a pH of 9.0 to about 10.5. The high alkalinity is necessary because oxidation occurs more readily in an alkaline system and at alkaline pH's, the hair softens and swells making it more receptive to the dye. The most commonly used alkali is ammonium hydroxide. Not only is it a good pH adjuster but it also is an effective swelling agent. Other additives such as alkylol amines can be used in addition to or in place of ammonia.

Finally, if desired a perfume can be added. A suitable perfume should be unaffected by the alkaline product and should be relatively unaffected by the peroxide during the short period of time that the dye bath is applied to the hair. Perfume compounds should be free of aldehydes which may react with amino compounds and cause difficulty.

In preparing the base composition, the ingredients (save for the pH adjuster and the perfume) are placed together in a suitable mixing vessel, heated to the necessary temperature generally about 50° to 175° Farenheit and stirred for about 20 to 60 minutes, generally about 30 minutes being sufficient. The base is then ready for the other components of the composition to be added thereto.

In addition to the base composition as well as the three essential ingredients to obtain the brown dye, other ingredients also included in the composition are modifiers and couplers. Modifiers and couplers are added to produce desirable color modifications as well as to serve as color stabilizers, antioxidants and retarders. For the purposes of this invention modifiers are defined as secondary dye intermediates which are hydroxylated aryl groups and include such compounds as pyrocatechol (1,2-benzenediol), resorcinol (1,3-benzenediol), chlororesorcinol, hydroquinone (1,4-benzenediol), pyrogallol (1,2,3-benzenetriol), phloroglucinol (1,3,5-benzenetriol), 1-naphthol, 1,3-dihydroxynaphthalene, 1,7-dihydroxynaphthalene, 2,7-dihydroxynaphthalene and glycin (N-(p-hydroxyphenyl)glycine). Of these modifiers those particularly valuable in this instance are resorcinol, 2,7-dihydroxynaphthalene, 1,7-dihyroxynaphthalene, pyrocatechol, phluroglucinol and glycin. Generally the modifier will be present in an amount of about 1.0 to 15.0 pbw and preferably 1.2 to about 11.0 pbw in the total composition. A particularly valuable combination (in 100 parts of total composition) contains:

0.30–2.50 pbw of 1,7-dihydroxynaphthalene,
0.20–1.00 pbw of 2,7-dihydroxynaphthalene,
0.20–2.00 pbw of resorcinol,
0.20–2.00 pbw of pyrocatechol,
0.20–2.00 pbw of phluroglucinol, and
0.10–1.50 pbw of glycin.

Suitable couplers include primary dye intermediates such as o- and p-aminophenols and suitable acid addition salts thereof such as the hydrochlorides and sulfates and secondary dye intermediates such as m-aminophenols. Generally the coupler is present at about 0.5–7.5 pbw and preferably 0.6–5.0 pbw. Particularly valuable are m-aminophenol, p-methylaminophenol sulfate, o-aminophenol, and the like. A particularly preferred modifier consists of 0.2–2.0 parts by weight of p-aminophenol,
0.2 to 2.0 parts by weight of p-methylaminophenol sulfate, and
0.2 to 1.5 o-aminophenol.

The composition of the invention is prepared by mixing the base as prepared as discussed hereinbefore with the essential ingredients and the modifiers and couplers at a temperature of about 50° to 200° Farenheit, preferably about 150° F. for a time sufficient to form a homogeneous mixture. This time will generally be less than two hours and usually will be ready in about one-half hour depending on the size of the batch which is being prepared.

The resulting composition is then mixed with a suitable oxidizing agent such as peroxide. Generally equal amounts of the dye composition are mixed with the peroxide as a 6% solution in water and the resulting mixture is then placed in contact with the hair which is to be dyed for a time sufficient to effect dyeing thereof. This will generally be about 20 to 60 minutes depending upon the depth which is desired. Generally the time will be about 30 minutes to 45 minutes. Thereafter the dye composition is washed off the hair so dyed.

Thus, a composition has been described which is essentially free of mutagenic phenylenediamines, derivatives thereof and nitro compounds. The composition is found to have little or no irritancy or sensitization and does not result in damage to the hair. It is easy to apply in a short period of time, has good stability and produces the illusion of natural color on the hair. It has a high degree of coverage, does not stain the scalp and is permanent under normal conditions. It is found to be fast to light, perspiration and shampooing.

Preparation of a Suitable Base

The following substances are measured and placed in a suitable mixing vessel

|  | Parts of Weight |
|---|---|
| Amidox L-2 | 7.00 |
| Propylene Glycol | 12.00 |
| Oleyl Alcohol | 10.00 |
| Glycerine | 6.00 |
| Igepal CO-430 | 4.00 |
| Carsonol ALS Spec. | 20.00 |
| Isopropyl Alcohol | 14.00 |
| Perfume | 0.30 |
| Sodium Sulfite | 0.20 |
| Trisodium EDTA | 0.10 |
| Water, Deionized | 20.40 |
| Ammonia 28% | 6.00 |
| TOTAL | 100.00 |

The mixture is heated to 150° for 30 minutes while stirring regularly until a homogeneous mixture is obtained. This mixture is then used to prepare the composition of the invention.

The following example is given as a representation of the composition of the invention but is not to be read in a limiting sense.

EXAMPLE 1

Preparation of a Composition of the Invention

The following amounts of ingredients are pre-weighed in a suitable vessel and added to sufficient quantity of the base prepared according to the above Preparation to make a total of a 100 gram mixture of a composition useful for a very dark brown hair dye.

| 1,5-dihydroxynaphthalene | 2.00 gm |
|---|---|
| p-aminodiphenylamine sulfate | 0.40 gm |
| m-aminophenol | 0.60 gm |
| p-methylaminophenol sulfate | 0.26 gm |
| 1,7-dihydroxynaphthalene | 1.80 gm |
| 2,7-dihydroxynaphthalene | 0.24 gm |
| o-aminophenol | 0.40 gm |
| resorcinol | 0.30 gm |

EXAMPLE 2

Preparation of a Composition of the Invention

The foilowing amounts of ingredients are pre-weighed in a suitable vessel and added to sufficient quantity of the base prepared according to the above Preparation to make a total of a 100 gram mixture of a composition useful for a dark brown hair dye.

| 1,5-dihydroxynaphthalene | 0.33 gm |
|---|---|
| p-aminodiphenylamine sulfate | 0.40 gm |
| m-aminophenol | 0.40 gm |
| p-methylaminophenol sulfate | 0.13 gm |
| 1,7-dihydroxynaphthalene | 0.47 gm |
| resorcinol | 0.40 gm |
| p-aminophenol | 0.40 gm |
| pyrocatechol | 0.26 gm |

EXAMPLE 3

Preparation of a Composition of the Invention

The following amounts of ingredients are pre-weighed in a suitable vessel and added to sufficient quantity of the base prepared according to the above Preparation to make a total of a 100 gram mixture of a composition useful for a dark warm brown hair dye.

| 1,5-dihydroxynaphthalene | 0.80 gm |
|---|---|
| p-aminodiphenylamine sulfate | 0.40 gm |
| m-aminophenol | 0.80 gm |
| p-methylaminophenol sulfate | 0.36 gm |
| 1,7-dihydroxynaphthalene | 0.80 gm |
| 2,7-dihydroxynaphthalene | 0.50 gm |
| p-aminophenol | 0.80 gm |
| pyrocatechol | 0.40 gm |

EXAMPLE 4

Preparation of a Composition of the Invention

The following amounts of ingredients are pre-weighed in a suitable vessel and added to sufficient quantity of the base prepared according to the above Preparation to make a total of a 100 gram mixture of a composition useful for a medium brown hair dye.

| 1,5-dihydroxynaphthalene | 0.60 gm |
|---|---|
| p-aminodiphenylamine sulfate | 0.25 gm |
| m-aminophenol | 0.50 gm |
| p-methylaminophenol sulfate | 0.20 gm |

| | |
|---|---|
| o-aminophenol | 0.40 gm |
| p-aminophenol | 0.60 gm |
| resorcinol | 0.20 gm |

EXAMPLE 5

Preparation of a Composition of the Invention

The following amounts of ingredients are pre-weighed in a suitable vessel and added to sufficient quantity of the base prepared according to the Above Preparation to make a total of a 100 gram mixture of a composition useful for a light golden brown hair dye.

| | |
|---|---|
| 1,5-dihydroxynaphthalene | 0.30 gm |
| p-aminodiphenylamine sulfate | 0.06 gm |
| m-aminophenol | 0.56 gm |
| p-methylaminophenol sulfate | 0.18 gm |
| o-aminophinol | 0.06 gm |
| p-aminophenol | 0.80 gm |
| phluroglucinol | 0.27 gm |
| glycin | 0.08 gm |
| pyrocatechol | 0.38 gm |

EXAMPLE 6

Equal quantities of the composition of each of Examples 1–5 are mixed with 6% aqueous hydrogen peroxide. The resulting mixture is applied to swatches of human hair for 30 minutes to give the followng results:

Example 1—Darkest Brown
Example 2—Dark Brown
Example 3—Warm Brown
Example 4—Medium Brown
Example 5—Light Golden Brown.

The subject matter claimed is:

1. A composition which, when combined with an oxidizing agent, dyes keratinous fibers brown, which composition is essentially free of o-, m- or p-phenylenediamine, 2,4-diaminoanisole and nitro compounds, said composition consisting essentially of:
about 0.1 to 4.0 parts by weight of 1,5-dihydroxynaphthalene;
about 0.01 to 1.5 parts by weight of p-aminodiphenylamine or a suitable acid addition salt thereof;
about 0.2 to 2.5 parts by weight of m-aminophenol;
about 1.0 to 15.0 parts by weight of a suitable modifier;
about 0.5 to 7.5 parts by weight of a suitable coupler;
a sufficient amount of a suitable dye base to make up a total of 100 parts by weight of said composition.

2. The composition of claim 1 wherein:
0.25 to 2.5 parts by weight of 1,5-dihydroxynaphthalene,
0.05 to 1.0 parts by weight of p-aminodiphenylamine or a suitable acid addition salt thereof; and
0.2 to 2.0 parts by weight of m-aminophenol are employed.

3. The composition of claim 1 or 2 wherein said modifier consists essentially of:
0.30–2.50 parts by weight of 1,7-dihydroxynaphthalene,
0.20–1.00 parts by weight of 2,7-dihdyroxynaphthalene,
0.20–2.00 parts by weight of resorcinol,
0.20–2.00 parts by weight of pyrocatechol,
0.20–2.00 parts by weight of phluroglucinol,
0.10–1.50 parts by weight of glycin.

4. The composition of claim 1 or 2 wherein said coupler consists essentially of:
about 0.2 to 1.5 parts by weight of o-aminophenol and about 0.2 to 2.0 parts by weight of p-aminophenol and about 0.2 to 2.0 parts by weight of p-methylaminophenol sulfate.

5. The composition of claim 1 wherein said dye base consists essentially of:
7.00 parts by weight of polyethylene glycol (3) lauryl amide,
12.00 parts by weight of propylene glycol,
10.00 parts by weight of oleyl alcohol,
6.00 parts by weight of glycerine,
4.00 parts by weight of polyethylene glycol p-nonylphenol ether having four ethylene glycol units,
20.00 parts by weight of ammonium lauryl sulfate
14.00 parts by weight of isopropyl acohol,
0.30 parts by weight of perfume,
0.20 parts by weight of sodium sulfite,
0.10 parts by weight of trisodium EDTA
20.40 parts by weight of deionized water, and,
6.00 parts by weight 28% aqueous ammonia.

6. The composition of claim 5 for dyeing hair a very dark brown, said composition consisting essentially of:
2.00 parts by weight of 1,5-dihydroxynaphthalene,
0.40 parts by weight of p-aminodiphenylamine sulfate,
0.60 parts by weight of m-aminophenol,
0.26 parts of weight of p-methylaminophenol sulfate,
1.80 parts of weight of 1,7-dihydroxynaphthalene
0.24 parts of weight of 2,7-dihydroxynaphthalene
0.40 parts of weight of o-aminophenol
0.30 parts of weight of resorcinol
94.8 parts of weight of the base of claim 5.

7. The composition of claim 5 for dyeing hair a dark brown, said composition consisting essentially of:
0.33 parts by weight of 1,5-dihydroxynaphthalene,
0.40 parts by weight of p-aminodiphenylamine sulfate,
0.40 parts by weight of m-aminophenol,
0.13 parts by weight of p-methylaminophenol sulfate,
0.47 parts by weight of 1,7-dihydroxynaphthalene,
0.40 parts by weight of resorcinol,
0.40 parts by weight of p-aminophenol,
0.26 parts by weight of pyrocatechol, and
97.21 parts of weight of the base of claim 5.

8. The composition of claim 5 for dyeing hair a dark warm brown, said composition consisting essentially of:
0.80 parts by weight of 1,5-dihydroxynaphthalene,
0.40 parts by weight of p-aminodiphenylamine sulfate,
0.80 parts by weight of m-aminophenol,
0.30 parts by weight of p-methylaminophenol sulfate,
0.80 parts by weight of 1,7-dihydroxynaphthalene,
0.50 parts of weight of 2,7-dihdyroxynaphthalene,
0.80 parts by weight of p-aminophenol,
0.40 parts by weight of pyrocatechol, and
95.2 parts by weight of base of claim 5.

9. The composition of claim 5 for dyeing hair a medium brown, said composition consisting essentially of:
0.60 parts by weight of 1,5-dihydroxynaphthalene,
0.25 parts by weight of p-aminodiphenylamine sulfate,
0.50 parts by weight of m-aminophenol,
0.20 parts by weight of p-methylaminophenol sulfate,
0.40 parts by weight of 1,7-dihydroxynaphthalene,
0.60 parts of weight of 2,7-dihydroxynaphthalene,
0.20 parts of weight of 0-aminophenol and
97.25 parts of weight of the bae of claim 5.

10. The composition of claim 5 for dyeing hair a light golden brown, said composition consisting essentially of:
0.30 parts by weight of 1,5-dihydroxynaphthalene,
0.06 parts by weight of p-aminodiphenylamine sulfate, 0.56 parts by weight of m-aminophenol,
0.18 parts by weight of p-methylaminophenol sulfate,
0.06 parts by weight of 1,7-dihydroxynaphthalene,
0.80 parts of weight of 2,7-dihydroxynaphthalene,
0.27 parts by weight of resorcinol,
0.08 parts by weight of p-aminophenol,
0.38 parts by weight of pyrocatechol, and
97.31 parts by weight of the base of claim 5.

11. A process for dyeing keratinous fibers brown, which process comprises contacting said fiber with an effective amount of a composition of claim 1 and an oxidizing amount of a suitable oxidizing agent for a time sufficient to effect dyeing.

12. The process of claim 11 wherin said keratinous fiber is human hair.

13. A hair dye composition consisting essentially of the composition of claim 1 and a suitable oxidizing agent.

* * * * *